United States Patent [19]

Verbruggen

[11] Patent Number: 4,849,511
[45] Date of Patent: Jul. 18, 1989

[54] TECHNETIUM CHELATES TO BE USED FOR DETERMINING THE RENAL FUNCTION

[75] Inventor: Alfons M. Verbruggen, Leuven, Belgium

[73] Assignee: Mallinckrodt, Inc., St. Louis, Mo.

[21] Appl. No.: 54,649

[22] Filed: May 26, 1987

[30] Foreign Application Priority Data

May 28, 1986 [NL] Netherlands ............... 8601369

[51] Int. Cl.[4] .................. C07F 13/00; A61K 49/02
[52] U.S. Cl. ............................ 534/14; 424/1.1
[58] Field of Search ..................... 424/1.1; 534/14

[56] References Cited

FOREIGN PATENT DOCUMENTS 0173424  3/1986  European Pat. Off. .

OTHER PUBLICATIONS

Taylor et al., "Preliminary Evaluation of TC-99M Mercaptoacetyl Triglycine", Contr. Nephrol., vol. 56, S. Taylor, 10/22/86, pp. 1-6.

*Primary Examiner*—John S. Maples
*Attorney, Agent, or Firm*—R. J. Klostermann; L. N. Goodwin

[57] ABSTRACT

The invention relates to a technetium chelate of the general formula

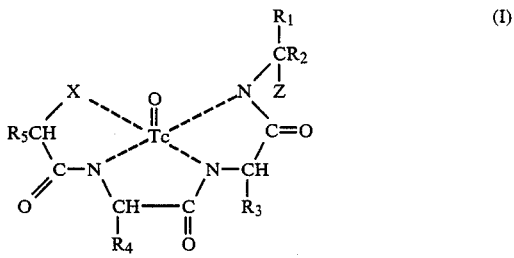

(I)

wherein
X is a sulphur atom or an imino group,
Z is a hydrogen atom, a carboxy group, an alkoxycarbonyl group having 1-4 carbon atoms, an aminocarbonyl group, a sulpho group, an aminousulphonyl group or a carboxymethylaminocarbonyl group,
Tc represents technetium-99m,
$R_1$ is a hydrogen atom or an alkyl group having 1 or 2 carbon atoms, and
$R_2$, $R_3$, $R_4$ and $R_5$ are equal or different and represent hydrogen atoms or branched or non-branched alkyl groups having 1-4 carbon atoms, which alkyl groups are optionally substituted with an amino group, a hydroxy group, a mercapto group, a halogen atom, a carboxy group or an aminocarbonyl group,
with the proviso that $R_3 R_4$ and $R_5$ do not all three of them represent hydrogen atoms;

as well as water-soluble salts of these compounds.

The invention also relates to a tripeptide compound to be used for preparing said chelate and to a kit comprising a composition of said tripeptide compound.

4 Claims, No Drawings

TECHNETIUM CHELATES TO BE USED FOR DETERMINING THE RENAL FUNCTION

The invention relates to a technetium chelate, as well as to a method of preparing said chelate, and to a tripeptide compound to be used therefor. The invention also relates to a radiopharmaceutical preparation comprising said chelate, to a kit therefor, and to the use of said preparation for diagnostic examination.

Radionuclide-labelled compounds are used for diagnostic examination, e.g. into deviations in shape and function of internal organs and into the presence and location of pathological processes in the body. For this purpose, a preparation in which the radioactive compound is present is administered to the patient, for example, in the form of an injectable liquid. By means of suitable detectors, e.g. a gamma camera, images can be obtained by recording the emitted radiation, of, for example, the organ or the pathological process in which the radioactive compound has been incorporated. Compounds generally used for examining the renal function are radioactive iodo-Hippuran and Tc99m-diethylene triamine pentaacetic acid (DTPA), which will be discussed hereinafter.

In addition to glomerular filtration, an active tubular secretion takes place in the kidneys. The functioning of the kidneys is determined for a considerable extent by the functioning of the kidney tubules. In an adult person approximately 125 ml of blood plasma per minute is purified by glomerular filtration. It is then said: the clearance is 125 ml per minute. The total clearance which can be effected by the kidneys is from 600 to 700 ml of plasma per minute. It appears from the clearance of 100 ml of blood plasma per minute which is found for the above-mentioned chelate of DTPA that said chelate is eliminated entirely or substantially entirely by glomerular filtration and is hence less suitable for examining the renel function.

An example of a radioactive iodo-Hippuran compound generally used for examining the renal function is iodo-131-Hippuran which, as is generally known, is secreted actively tubularly and is hence very suitable for examining the renal function as regards organ specificity.

There is a great need for a suitable preparation for examining the renal function which is permanently available, in particular for kidney transplantation patients, victims of accidents and patients after large vascular operations.

The above-mentioned iodo-131-Hippuran would be excellently suitable for these applications, also due to its good availability. However, like all iodo-131-compounds, iodo-131-Hippuran constitutes a severe radiation burden for the patient. Therefore, this iodo-131-compound can be administered to the patient only in a restricted dose, as a result of which the resulting information is insufficient to obtain statistically reliable images of the renal function by means of a gamma camera.

Another radioactive iodo-Hippuran compound which is much used for examining the renal function is iodo-123-Hippuran which is excellently suitable as regards the organ specificity and the restricted radiation burden. However, iodo-123-containing preparations have a restricted availability due to the short half-life, namely 13.3 hours, and the production of iodo-123 which necessarily has to be carried out in a cyclotron.

Technetium complexes which do have a tubular secretion which is comparable to that of iodo-Hippuran are known from European patent application 0.173.424. This application discloses inter alia the preparation of Tc99m-mercaptoacetylglycylglycylglycine (Tc99m-MAG3), which complex is secreted by the kidneys selectively and slightly faster than iodo-Hippuran. Other derivatives, such as Tc99m-MAGG-alanine and Tc99m-MAGG-asperagine, also show comparably good secretion characteristics.

However, the organ specificity still leaves to be desired, as will become apparent from the specific examples. In practice this is considered to be a disadvantage, the more so because these compounds are used for function examination.

New Tc99m-compounds have now surprisingly been found which are secreted very rapidly tubularly by the kidneys and in which the above disadvantage is hence mitigated. These compounds have the general formula:

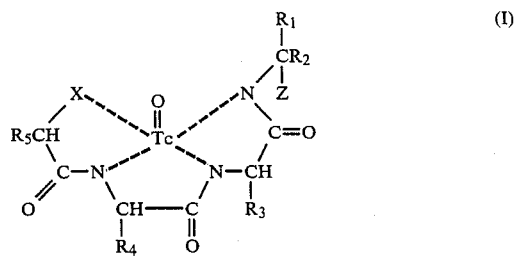

wherein

X is a sulphur atom or an imino group,

Z is a hydrogen atom, a carboxy group, an alkoxycarbonyl group having 1-4 carbon atoms, an aminocarbonyl group, a sulpho group, an aminosulphonyl group or a carboxymethylaminocarbonyl group, Tc represents technetium-99m, $R_1$ is a hydrogen atom or an alkyl group having 1 to 2 carbon atoms, and $R_2$, $R_3$, $R_4$ and $R_5$ are equal or different and represent hydrogen atoms or branched or non-branched alkyl groups having 1-4 carbon atoms, which alkyl groups are optionally substituted with an amino group, a hydroxy group, a mercapto group, a halogen atom, a carboxy group or an aminocarbonyl group, with the proviso that $R_3$, $R_4$ and $R_5$ do not all three of them represent hydrogen atoms;

as well as water-soluble salts of these compounds.

To be preferred are compounds of the general formula I, wherein

X is a sulphur atom,

Z is a carboxy group or an alkoxycarbonyl group having 1-4 carbon atoms,

Tc is technetium-99m, $R_1$ and $R_2$ represent hydrogen atoms, and $R_3$, $R_4$ and $R_5$ are equal or different and represent hydrogen atoms, methyl groups, ethyl groups, isopropyl groups, aminomethyl groups, hydroxymethyl groups, mercaptomethyl groups or halomethyl groups, with the proviso that $R_3$, $R_4$ and $R_5$ do not all three of them represent hydrogen atoms;

as well as water-soluble salts of these compounds.

Still more preferred are compounds of the general formula I, wherein

X, Z, Tc, $R_1$ and $R_2$ have the last-mentioned meanings, and $R_3$, $R_4$ and $R_5$ are equal or different and represent hydrogen atoms, methyl groups or hydroxymethyl groups, with the proviso that at least one of the symbols $R_3$, $R_4$ and $R_5$ represents a methyl group;

as well as water-soluble salts of these compounds.

Compounds of the general formula I, wherein

X, Z, Tc, $R_1$ and $R_2$ again have the last-mentioned meanings, $R_3$ is a methyl group or a hydroxymethyl group, and $R_4$ and $R_5$ are hydrogen atoms, as well as water-soluble salts of these compounds have appeared to be eminently suitable for the intended use.

The new compounds of the invention can be prepared in a manner known per se for the preparation of related compounds. So the new compound of formula I can be prepared in that technetium-99m in the form of a pertechnetate is reacted, in the presence of a reducing agent and optionally a suitable exchanging ligand, with a tripeptide compound of the general formula

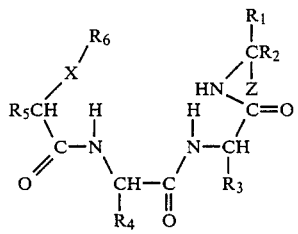

wherein

X, Z, $R_1$, $R_2$, $R_3$, $R_4$ and $R_5$ have the meanings given in claim 1, and $R_6$ is a hydrogen atom or a suitable protective group, preferably in a substantially aqueous medium at a temperature between 0° C. and 100° C. Suitable protective groups are acylgroups or acylaminoalkyl groups, like acetyl, benzoyl, acetylaminomethyl, trifluoroacetyl, hydroxyacetyl and carboxyacetyl.

The invention also relates to new tripeptide compounds, which may be used to prepare the above-mentioned new Tc99m-compounds. These new tripeptide compounds have the general formula:

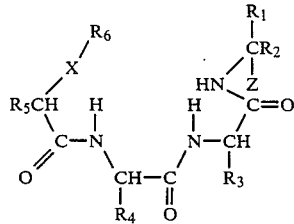

wherein

X, Z, $R_1$, $R_2$, $R_3$, $R_4$ and $R_5$ have the above meanings, and $R_6$ is a hydrogen atom or a suitable protective group. Suitable protective groups are disclosed in the European patent application No. 0.173.424 mentioned hereinbefore and are defined above. The new tripeptide compounds can be prepared in a manner known per se for the preparation of related compounds. So the new tripeptide compound of formula II can be prepared by reacting a compound of the general formula

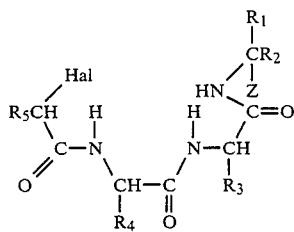

wherein Z, $R_1$, $R_2$, $R_3$, $R_4$ and $R_5$ have the above meanings, and

Hal is a halogen atom, with a compound of the general formula

wherein

M represents alkali metal, and

X and $R_6$ have the above meanings, preferably in an organic solvent at a reaction temperature between 0° C. and the boiling point of the solvent.

Preferably, however, the new tripeptide compounds can be prepared by reacting a tripeptide of the general formula

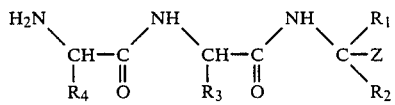

with a compound of the general formula

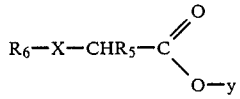

wherein $R_1$, $R_2$, $R_3$, $R_4$, $R_5$, $R_6$, X and Z have the above meanings, and Y is an activating group. A suitable activating group is a succinimido group. The latter route for synthesizing the tripeptide compound is preferably carried out in a polar solvent or solvent mixture at ambient or increased temperature. This reaction should be understood to also include use the appropriate amino acid or dipeptide as starting material, the product obtained being subsequently converted to the desired tripeptide compound by the usual peptide synthesis.

The new tripeptide compounds may occur in optical isomers which, if desired, can be separated by means of methods known for that purpose. The biological properties of different diastereoisomeric Tc99m-compounds prepared from these isomeric tripeptide compounds may differ. The quantity of the desired diastereoisomeric Tc99m-compound in the isomeric mixture may be influenced by suitably adjusting the reaction conditions, e.g. the pH, during the preparation process; this will be clear from the Examples.

The tripeptide compounds according to the invention are usually processed to compositions suitable for diagnostic purposes. When the composition is to be used for the preparation of a Tc99m-containing radiopharmaceutical preparation, starting from Tc99m-pertechnetate, the composition should comprise a reducing agent, for example, a dithionite or stanno-ions, optionally complexed with an exchange ligand, for example, a tartrate. Such a composition with a suitable reducing agent can also be prepared in a sterile manner in a lyophilized form. Finally the invention relates to a kit which is suitable for the preparation of a radiopharmaceutical prepration and which comprises the said composition.

The invention will now be described in greater detail with reference to the ensuing specific examples.

EXAMPLE I

Synthesis of benzoylmercaptoacetylglycyl-D-alanylglycine-ethyl ester

Succinimidyl-N-(S-benzoylmercaptoacetyl)glycinate is prepared according to the method described by R. F. Schneider et al, Journal of Nuclear Medicine 25 (2), 223-229 (1984). Glycyl-D-alanine in an amount of 250 mg is dissolved in 15 ml of water and the mixture is heated to 70° C. on a water bath. Meanwhile, 1 g of succinimidyl-N-(S-benzoylmercaptoacetyl)glycinate is dissolved in 40 ml of ethanol and the mixture is heated to 70° C. on a water bath. The solution of glycyl-D-alanine in water is added at once to the said ethanolic solution while stirring magnetically. The mixture is then refluxed for 1 hour. After cooling, the solution is evaporated to dryness under reduced pressure. The solid residue is shaken five times with 15 ml of acetone which is each time filtered off. Benzoylmercaptoacetylglycyl-D-alanine is precipitated from the collected filtrates by the addition of diethylether. The precipitate is filtered off and dried in vacuo over phosphorous pentoxide. In this manner 174 mg (yield 31.6%) of benzoylmercaptoacetylglycyl-D-alanine are obtained as a white crystalline powder. Benzoylmercaptoacetylglycyl-D-alanine in an amount of 150 mg is dissolved in 40 ml of tetrahydrofuran and the solution is cooled in an ice bath at 0° C. A solution of 50 mg of glycine-ethyl ester and 100 mg of dicyclohexylcarbodi-imide in 15 ml of tetrahydrofuran is slowly added while stirring magnetically. The mixture is stirred at 0° C. for 2 hours and then at room temperature for 15 hours. The resulting precipitate is then filtered off and the filtrate is evaporated to dryness under reduced pressure. The solid residue is shaken with a mixture of 50 ml of water and 50 ml of methylene chloride. The organic layer is separated, dried over anhydrous sodium sulphate and evaporated to dryness in vacuo. The solid residue is shaken five times with 15 ml of acetone which is each time filtered off. The collected filtrates are concentrated in vacuo to 15 ml and diethylether is added dropwise thereto while stirring until complete formation of precipitate. The precipitate is filtered off, washed with diethyl ether and dried over phosphorous pentoxide in vacuo. In this manner, 155 mg (55.1% yield) of benzoylmercaptoacetylglycyl-D-alanylglycine ethyl ester are obtained. The identity of this compound is confirmed by mass spectrometry, proton-NMR analysis and elementary analysis: mp 137° C.; $[\alpha]_D^{20}$+20.5 (C=1 in methanol); mass spectrum m/e− 410; nmr (DMSO-d6): δ1.22 (3H, d, CH$_3$), 3.77 (2H, d, δ—CH$_2$—N), 3.81 (2H, d, α—CH$_2$—N), 3.87 (2H, s, CH$_2$—S), 4.33 (1H, q, β—CH), 8.08 (1H, d, β —NH), 8.28 (1H, t, α—NH), 8.42 (1H, t, δ—NH), 7.5-8.04 (5H, complex, aromatic), 4.08 (2H, q, OCH$_2$), 1.18 (3H, t, ester—CH$_3$).

EXAMPLE II

Preparation of Tc99m-mercaptoacetylglycyl-D-alanyl-glycine

Benzoylmercaptoacetylglycyl-D-alanylglycine ethyl ester in an amount of 1 mg is provided in a glass bottle and 740 Megabecquerel of Tc99m in the form of sodium pertechnetate in 1 ml of physiological saline solution (obtained from an Mo99/Tc99m generator) and 40 microliters of 5.0 normal sodium hydroxide are added. The mixture is heated in a boiling water bath for 3 minutes and 3 mg of sodium dithionite in 0.1 ml of water are then added and mixed. The mixture is heated for another 2 minutes in a boiling water bath. After the addition of 30 microliters of 6.0 normal hydrochloride acid and cooling, the solution is filtered through a 0.22 micrometer filter. In addition to small quantities of impurities, the filtrate comprises substantially Tc99m-mercaptoacetylglycyl-D-alanylglycine in the form of 2 diastereoisomers the relative quantities of which may vary in accordance with the particular conditions during the labelling reaction. The isomers can be isolated by high-pressure liquid chromatography (HPLC) using a 0.25 inch×25 cm column filled with ODS (a silica-containing carrier, pretreated with octadecylsilane; 10 micrometers grain diameter) as a stationary phase and an eluent composed of 92 parts by volume of 0.05 molar phosphate buffer pH 6 and 8 parts by volume of ethanol. With a supply of 1.0 ml per minute, the first diastereoisomer (component A or Tc99m-MAGAG-DA) is eluted after approximately 7 minutes and the second diastereoisomer (component B of Tc99m-MAGAG-DA) after approximately 11 minutes. These retention times may vary slightly according to the specific characteristic features of each individual column and according to the origin of the ODS filling material.

EXAMPLE III

Biodistribution of Tc99m-mercaptoacetylglycyl-D-alanylglycine in mice

Tc99m-MAGAG-DA, separated by HPLC, is diluted with physiological saline solution to a concentration of 370 kilobecquerel per ml. Iodo-131-Hippuran is added to this solution as a reference standard. An amount of 0.1 ml of this mixture is injected intravenously into each of the eight mice, so that 37 kilobecquerel of Tc99m-MAGAG-DA and 18.5 kilobecquerel of iodo-131-Hippuran are injected per animal. Measures are taken to collect all the excreted urine. 10 Minutes after the administration the mice are sacrificed. It is ensured that all the blood is collected. All parts of the body are brought in separate tubes and the activity of Tc99m and I131 is determined for each part of the body. From the measured results the relative quantity of both tracer products in urine, kidneys, intestines, liver, blood and the collective remainder of the body is computed. In the same manner, Tc99m-MAGAG-DB, separated by HPLC, and Tc99m-mercaptoacetylglycylglycylglycine (Tc99m-MAG3), purified by HPLC, both with iodo-131-Hippuran as a reference standard, are tested in two other groups of 8 and 6 mice, respectively. For all three Tc99m-labelled compounds —MAGAG-DA, MAGAG-DB and MAG3— the relative percentages of Tc99m activity in the various organs are calculated with respect to iodo-131-Hippuran. After this, the ratios of Tc99m-MAGAG-DA and -DB can be calculated with respect to Tc99m-MAG3 in the various organs. The results are recorded in Table A below.

TABLE A

Biodistribution after 10 minutes of Tc99m-MAGAG-DA and MAGAG-DB relative to Tc99m-MAG3 in mice. (results are expressed as ratios)

| Organ | uptake of Tc-99m-MAGAG-DA / Tc-99m-MAG3 | Tc99m-MAGAG-DB / Tc99m-MAG3 |
|---|---|---|
| Urine | 1.13 | 1.14 |
| Kidneys | 0.36 | 0.37 |
| Liver | 0.68 | 0.68 |
| Intestines | 0.44 | 0.41 |
| Stomach | 0.83 | 0.85 |
| Blood | 1.12 | 1.20 |
| Remainder | 0.90 | 0.94 |
| Renal | 1.05 | 1.07 |
| Hepatic | 0.60 | 0.59 |

From these data it appears that the secretion characteristics for Tc99m-MAGAG-DA and -DB do not differ significantly and are both significantly better than those of Tc99m-MAG3 as regards the faster secretion in the urine and the lower retention in kidneys, liver and intestines.

EXAMPLE IV

Preparation of S-benzoylmercaptoacetylglycyl-D-serylglycine (D-MAGSERG)

7.72 g of carbobenzyloxy-D-serylglycine benzylester, synthesized as described by Fölsch in Acta Chim. Scand. 12, 501 (1958), is dissolved in 150 ml of methanol. After addition of 0.2 ml of glacial acetic acid and 0.5 g of palladium on activated carbon (10% Pd) the mixture is hydrogenated in a Parr-apparatus at a hydrogen pressure of 45 psi during 6 hours. The solvent is removed under reduced pressure, 50 ml of water are added to the residue and the mixture is stirred during 30 min. The catalysator is removed by filtration and the filtrate evaporated under reduced pressure. The residue is suspended in 20 ml of ethanol and the precipitate is collected by filtration and washed successively with ethanol, acetone and diethylether. After drying over phosphorous pentoxide under vacuum 1.97 g of D-serylglycine is obtained (yield 92%) as a slightly greenish powder.

To a solution of 6.4 succinimidyl-N-(S-benzoylmercaptoacetyl)glycinate in 40 ml of ethanol at 70° C. is added in one portion a solution of 1.008 g of the above D-serylglycine in 10 ml of water at 70° C. The reaction mixture is refluxed for 1 hour and then stirred at room temperature overnight. After evaporation of the solvents the residue is agitated with 25 ml of acetone. The precipitate is removed by filtration. Diethylether is added to the filtrate until precipitation is complete. The precipitate is collected by filtration and washed with diethylether. After drying 1.56 g of a yellowish powder is obtained. To 600 mg of this is added 15 ml of chilled methanol. After agitation during 5 min. the white precipitate is filtered off, washed with cold methanol and dried to obtain 400 mg of S-benzoylmercaptoacetylglycyl-D-serylglycine as a white powder, m.p. 149° C. N.M.R. (DMSO-d6): δ 3.61 (2H, d, $CH_2$—OH), 3.77 (2H, d, α—$CH_2$—N), 3.84 (2H, d, δ—$CH_2$—N), 3.88 (2H, s, S—$CH_2$), 4.38 (1H, dt, CH), 8.03 (1H, d, β—NH), 8.17 (1H, t, α—NH), 8.44 (1H, t, γ—NH).

EXAMPLE V

Preparation of S-benzoylmercaptoacetyl-D-alanylglycylglycine (MAAG2)

To a solution of 1 g of succinimidyl-N-(S-benzoylmercaptoacetyl)glycinate in 25 ml of anhydrous ethanol at 70° C. is added in one portion a solution of 203 mg of D-alanylglycylglycine in 10 ml of water at 70° C. The reaction mixture is refluxed for 1 hour and the solvents are evaporated under reduced pressure. The residue is agitated with 5 portions of 25 ml acetone, which is isolated by filtration. The combined filtrates are treated with diethylether until precipitation is complete. The precipitate is filtered off, washed with diethylether and dried over $P_2O_5$ under vacuum to obtain 170 mg (47,7%) of S-benzoylmercaptoacetyl-d-alanylglycylglycine as a white powder, m.p. 167°-170° C. $[\alpha]_D^{20}+22$ (c=1 in methanol); nmr (DMSO-d6): δ 1.24 (3H, d, $CH_3$), 3.88 (2H, s, $CH_2$—S), 3.74 (4H, d, $2 \times CH_2$—N), 4.31 (1H, q, CH), 8.08 and 8.24 (each 1H, t, α— and β—NH), 8.51 (1H, d, δ—NH), 7.5–8.04 (5H, complex, aromatic).

EXAMPLE VI

Preparation of S-benzoyl-D-2-mercaptopropionyl glycylglycylglycine (MPG3)

To a solution of 4.38 g sodium in anhydrous methanol is added a solution of 27.5 g freshly distilled thiobenzoic acid in 50 ml of methanol. The resulting solution of sodium thiobenzoate is added dropwise to a mixture of 14.15 g L-2-bromopropionic acid and 50 ml methanol. The reaction mixture is refluxed for 90 min., acidified to pH 2.5 with 3N HCl and evaporated to dryness. The residue is extracted twice with 50 ml of ethylacetate. The combined organic layers are washed with water, dried on anhydrous sodium sulphate and evaporated under reduced pressure. 5 g of the resulting brown oil are purified by column adsorption chromatography on silica gel with chloroform as the eluent to yield 1.2 g of a yellow oil (S-benzoyl-L-2-mercaptopropionic acid); 1.05 g of this oil is converted to the succinimide ester and coupled with glycylglycylglycine following the procedure described for MAG3 by Schneider et al. (J. Nucl. Med., 25, 223–229, 1984). In this way 265 mg of D-(S)-benzoyl-2-mercaptopropionyl glycylglycylglycine is obtained as a white powder. m.p. 174° C.; $[\alpha]_D^{20}+55.5$ (C=1 in methanol); nmr (DMSO-d6): δ 1.48 (3H, d, $CH_3$), 3.74 (6H, d, $3 \times CH_2$—N), 4.22 (1H, q, CH), 8.13 (2H, t, α+β—NH), 8.48 (1H, t, γ—NH), 7.5–8.04 (5H, complex, aromatic).

EXAMPLE VII

Preparation of Tc99m-mercaptoacetylglycyl-D-serylglycine (Tc99m-MAGSERG-D)

Procedure 1:

In a 10 ml-vial are mixed 0.5 mg S-benzoylmercaptoacetylglycyl-D-serylglycine, 0.2 ml of acetate buffer solution pH 5.0, 15 μl of a 0.2% m/V solution of $SnCl_2.2H_2O$ in HCl 0.05 N, 2 ml of ($^{99m}$Tc)-sodiumpertechnetate in saline containing 370 to 740 MBq of Tc99m. The vial is heated in a water bath for 10 min. and allowed to cool to room temperature. The diasteroisomers in the reaction mixture are isolated by HPLC on a 25 cm×0.25 inch Zorbax RP 18 column (octadecylsilyl) eluted in an isocratic way with a mixture of 0.06 M phosphate buffer pH 5.85 and ethanol (96:4). At a flow rate of 1 ml/min. the retention times of isomer A and B are respectively 3.8 min. and 5.9 min. The relative amounts of isomer A and B are respectively 52% and 48%.

In the same way Tc99m-mercaptoacetyl-D-alanyl-glycylglycine (Tc99m-MAAG2-DB) and Tc99m-D-2-mercaptopropionylglycylglycylglycine (Tc99m-MPG3-DB) are prepared from MAAG2 and MPG3, obtained according to Examples V and VI respectively.

Procedure 2:

The procedure is the same as the previous one, except for the acetate buffer (pH 5.0) that is replaced by a phosphate buffer pH 8.45. In this way the final relative amounts of isomers A and B are respectively 95% and 5%.

EXAMPLE VIII

Biodistribution of Tc99m-MAAG2-DB in mice.

In the same way as described in Example III the biodistribution of the above compound in mice is determined relative to that of Tc99m-MAG3 by organ uptake measurements. The results are recorded in table B below.

TABLE B

Biodistribution of Tc99m-MAAG2-DB relative to Tc99m-MAG3 in mice (results are expressed as ratios between organ uptake of this compound and of Tc99m MAG3)

| Organ | uptake Tc99m-MAAG2-DB / uptake Tc99m-MAG3 |
| --- | --- |
| Urine | 0,99 |
| Kidneys | 0.66 |
| Liver | 0.79 |
| Intestines | 0.95 |
| Stomach | 1.40 |
| Blood | 1.17 |
| Rest | 1.45 |
| Renal system | 0.96 |
| Hepatic system | 0.84 |

From the above data it appears that Tc99m-MAAG2-DB shows a more favourable organ distribution than Tc99m-MAG3 in that kidneys and liver obtain less radioactivity, while the secretion in the urine is comparably fast.

EXAMPLE IX

Biodistribution of Tc99m-MAGSERG-DA and MAGSERG-DB in mice

In the same way as described in Example III the biodistribution of the above compound in mice is determined relative to that of Tc99m-MAG3 by organ uptake measurements. The results are recorded in table C below.

TABLE C

Biodistribution of Tc99m-MAGSERG-DA and Tc99m-MAGSERG-DB, relative to Tc99m-MAG3, in mice (results are expressed as ratios)

| Organ | uptake of Tc99m-MAGSERG-DA / Tc99m-MAG3 | Tc99m-MAGSERG-DB / Tc99m-MAG3 |
| --- | --- | --- |
| Urine | 1.13 | 1.10 |
| Kidneys | 0.44 | 0.42 |
| Liver | 0.39 | 0.72 |
| Intestines | 0.48 | 0.47 |
| Stomach | 0.70 | 0.66 |
| Blood | 0.98 | 0.94 |
| Rest | 1.38 | 1.23 |
| Renal system | 1.03 | 1.01 |
| Hepatic system | 0.43 | 0.67 |

From the above data it appears that the secretion characteristics for Tc99m-MAGSERG-DA and -DB differ slightly but are both significantly better than those of Tc99m-MAG3 as regards the faster secretion in the urine and the lower retention in kidneys, liver and intestines.

I claim:

1. A compound of the general formula

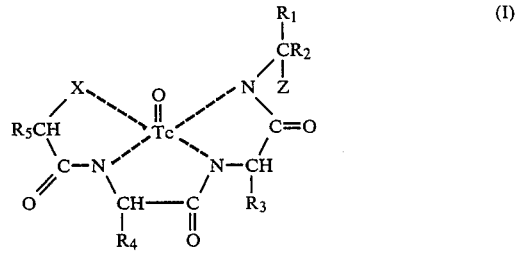

wherein

X is a sulphur atom or an imino group,

Z is a hydrogen atom, a carboxy group, an alkoxycarbonyl group having 1–4 carbon atoms, an aminocarbonyl group, a sulpho group, an aminosulphonyl group or a carboxymethylaminocarbonyl group, Tc represents technetium-99m, $R_1$ is a hydrogen atom or an alkyl group having 1 or 2 carbon atoms, and $R_2$, $R_3$, $R_4$ and $R_5$ are equal or different and represent hydrogen atoms or branched or non-branched alkyl groups having 1–4 carbon atoms, which alkyl groups are optionally substituted with an amino group, a hydroxy group, a mercapto group, a halogen atom, a carboxy group or an aminocarbonyl group, with the proviso that $R_3$, $R_4$ and $R_5$ do not all represent hydrogen atoms;

as well as water-soluble salts of these compounds.

2. A compound as claimed in claim 1, of the general formula I, wherein

X is a sulphur atom,

Z is a carboxy group or an alkoxycarbonyl group having 1–4 carbon atoms,

Tc is technetium-99m, $R_1$ and $R_2$ represent hydrogen atoms, and $R_3$, $R_4$ and $R_5$ are equal or different and represent hydrogen atoms, methyl groups, ethyl groups, isopropyl groups, aminomethyl groups, hydroxymethyl groups, mercaptomethyl groups or halomethyl groups, with the proviso that $R_3$, $R_4$ and $R_5$ do not all represent hydrogen atoms;

as well as a water-soluble salt of this compound.

3. A compound as claimed in claim 1, of the general formula I, wherein

X, Z, Tc, $R_1$ and $R_2$ have the meanings given in claim 2, and $R_3$, $R_4$ and $R_5$ are equal or different and represent hydrogen atoms, a methyl groups or hydroxymethyl groups, with the proviso that at least one of the symbols $R_3$, $R_4$ and $R_5$ represents a methyl group; as well as a water-soluble salt of this compound.

4. A compound as claimed in claim 1, of the general formula I, wherein

X, Z, Tc, $R_1$ and $R_2$ have the meanings given in claim 2, $R_3$ is a methyl group or a hydroxymethyl group, and $R_4$ and $R_5$ are hydrogen atoms;

as well as a water-soluble salt of this compound.

* * * * *